United States Patent [19]

Sharpe et al.

[11] Patent Number: 4,989,307
[45] Date of Patent: Feb. 5, 1991

[54] APPARATUS FOR FACILITATING OF THE REMOVAL AND DISPOSAL OF MEDICAL NEEDLES

[76] Inventors: Kenneth M. Sharpe, 14791 E. Colgate Dr., Aurora, Colo. 80014; Mary A. Sharpe, 1116 W. 7th, Columbia, Tenn. 38401

[21] Appl. No.: 350,501
[22] Filed: May 11, 1989
[51] Int. Cl.[5] .............................................. B65D 25/00
[52] U.S. Cl. ..................................... 29/240; 206/366; 128/917
[58] Field of Search ................ 206/365, 366; 128/917; 29/240, 240.5, 239, 280, 282; 81/57.38

[56] References Cited
U.S. PATENT DOCUMENTS 4,375,849 3/1983 Hanifl .................................... 206/366
4,807,344 2/1989 Kelson et al. ........................... 29/240

Primary Examiner—Robert C. Watson
Attorney, Agent, or Firm—Timothy J. Martin

[57] ABSTRACT

An apparatus for removing and disposing of a needle assembly used for blood sampling with a minimum of manipulation and without contact with a contaminated part. The needle assembly includes a needle portion and a hub, the hub is adapted for cooperative engagement with the medical device such that the assembly is attached for use in drawing blood samples. The apparatus for removal and disposing of used needles assemblies includes a hub rotating mechanism for coupling with and rotating the hub about its longitudinal axis to cause the needle assembly to become detached from the medical device. Furthermore, the apparatus has a hub locator for maintaining the hub of the needle assembly in a fixed location and orientation so the hub is coupled with the hub rotating mechanism to cause the needle assembly to rotate and become detached from the medical device. The needle assembly is stored in an enclosure operative to receive and protectively enclose the needle assembly after it is detached from the medical device.

24 Claims, 6 Drawing Sheets

APPARATUS FOR FACILITATING OF THE REMOVAL AND DISPOSAL OF MEDICAL NEEDLES

TECHNICAL ARENA

The present invention relates to the disposal of needles used for medical purposes. More specifically, the present invention relates to the disposal of needle assemblies used for parenteral and other medical procedures and particularly to the removal of phlebotomy needle assemblies from their associated medical devices and disposal of the phlebotomy needle assemblies

BACKGROUND OF THE INVENTION

An increasingly serious threat to health care personnel in general, and most specifically to health care technicians who regularly draw blood from patients for analytical purposes, is the possible contraction of an infectious disease from an incidental needle prick or the puncturing or scratching of the skin by any of a variety of medical cutting and puncturing devices. Handling of parenteral and phlebotomy needle assemblies during disposal procedures after they are used is considered to present one of the most serious risks of job injury to health care workers.

Federal regulations require used medical needles be disposed of in the safest possible manner. A great variety of devices have been offered or suggested to facilitate and improve the safety of medical needle disposal. Most commonly, these devices are one of two types, a first class of devices incorporating needle removal and a second class of devices incorporating needle severance. While needle severance devices may be adapted to work with both medical units having needle assemblies with removable hubs and units having fixed integral needle elements, an inherent problem with the use of devices relying upon needle severance is the residual sharp stump of the needle which remains with the needle assembly hub or barrel of an integral parental syringe or other device, which poses a latent threat of skin piercing injury. A greater, more obvious thread is posed where the second needle of double ended needle assemblies, such are is used with phlebotomy devices which utilize vacuum sample containers to withdraw blood samples, are not severed and remain with the device.

Most medical needle assemblies presently used at health care facilities are detachable from the associated medical device at the needle assembly hub. The detachable joining of the medical device and the needle assembly at the hub is generally accomplished by use of helical threads or friction retention male/female couplings. Particularly in the case of double ended phlebotomy needles used with vacuum sample vials, the detachable hubs may be provided with a helical thread. Thus a number of devices have been suggested and made available for removing and disposing of needle assemblies utilizing detachable hubs, particularly those incorporating a helical thread.

Needle disposal devices have been available for use with both threaded and friction-fit removable hub needle assemblies which incorporate a container with a lid which includes a hole contiguous with a tapered slot to allow the hubs to be jammed in the tapered slot and removed by manual manipulation of the medical unit. Similar devices, for use exclusively with threaded hubs, have utilized a stair-stepped edge along the slot to engage ribs on the threaded hub in a manner similar to a hub wrench. Many of these devices require the use of both hands, one to hold the body of the device and the other to position the hub of the medical unit in the hole, engage it in the converging slot and rotate the barrel of the syringe or other medical device attached to the needle assembly to cause the helical threads of the hub to become disengaged. Often, with these devices, the hub must be urged from the converging slot back toward the hole with the barrel of the syringe or body of the medical device before it will drop into the disposal container. Some of the devices available incorporate a bracket to attach the container to a fixed surface and thus allow needle assemblies to be disposed of with one hand. However, while these devices allow one hand to be free, one handed manipulation of the medical device nonetheless requires time and a minimum degree of dexterity and presents a risk of fumbling the medical unit resulting in a scratch or puncture of the skin by the needle.

Many needle disposal devices also incorporate large openings in their lids to allow their uses as mini medical trash receptacles. Such holes compromise the protection offered by these units by remitting fingers to extend into the container holding the contaminated needles thus increasing the risk of personal injury. Also, when the container is not fastened in place and may be tipped or knocked over, such large openings may allow used needles to spill from the container, again presenting a hazard of skin scratches or punctures by used needles.

DISCLOSURE OF THE INVENTION

It is an object of the present invention to facilitate the disposal of a wide variety of medical needles. It is particularly an object of the present invention to facilitate the disposal of both single needle assemblies, such as parenteral needle assemblies, and double needle assemblies, such as many phlebotomy needle assemblies.

It is an object of the present invention to provide for the quick and safe removal of needle assemblies from associated medical devices to allow separate disposal of the needles and the medical devices.

Yet a further object of the present invention is to provide for the needle assemblies to be removed safely from the medical device using only one hand. It is an object of the present invention to require minimum of manual manipulation of the medical unit to remove the needle assemblies so that use of the invention does not require great manual dexterity. A particular object of the present invention is to allow removal of helical threaded hub needle assemblies with one hand without need for great manipulative dexterity.

Also, it is an object of the present invention to immediately isolate the needle assembly upon removal of the needle assembly from the medical device. An additional object is to provide a protective enclosure for the needle device once it is removed.

Also, it is an object of the present invention to provide for removal and disposal of friction fit hub needle assemblies with the same disposal unit utilized for the removal of helical hub assemblies.

Also an object of the present invention is to collect the removed needles in a protective container which can be easily and safely handled and disposed of once full.

In keeping with the above objects, the present invention facilitates the removal of medical needle assemblies from medical devices with which they have been used in combination as medical units and disposal of the needle assemblies after their removal. A preferred embodiment of the removal and disposal device of the present invention has a base assembly, including a base and a pillar structure, supporting a head structure. A removable container for protectively enclosing needle assemblies once they are removed from medical units is insertable between the head structure and the base, where it is releasably retained by a latch assembly. The head structure includes a rotatable member which has a central aperture and is provided with a chuck to close upon and couple with the hub of a needle assembly located within the central aperture of the member when the member is rotated. A locating device above the rotating member includes a funnel-like member converging to an aperture which is sized such that, when a needle assembly of a medical unit is inserted through the funnel, the barrel or body of the medical device will not pass through the aperture and the hub of the needle assembly of the medical unit is held in a fixed location within the central aperture of the rotating member. A switch is provided to energize an electric motor and rotate the member in a direction such that, when the hub is engaged by the chuck, the hub will become detached from the medical device. A passage is located beneath the aperture of the rotating member which leads to an opening in the top of a disposal container so that, when the motor is de-energized, causing the member to cease rotation and the chuck to open and release the needle assembly hub, the needle assembly drops through the passage and enters the container where it is retained in the protective enclosure. The removable container includes a hinged lid which, when the container is filled to capacity, may be closed over the opening. A recessed area on the top of the container, of the same shape and size as the lid, surrounds the opening and is provided with a wall about its perimeter which engages and fixes the edge of the lid in place when it is pressed into its closed position. Thus, the needle assemblies may be sealed in the container for safe and convenient disposal.

In an alternative embodiment, needle assemblies are provided with lugs extending outwardly from the hub axis to terminate at free distal ends. Coupling extensions extend inwardly from an interior surface of the aperture and act against the distal ends of the lugs when the hub is introduced into the aperture and the rotatable member is rotated.

In yet another embodiment of the invention, the rotating member has an exterior surface which engages an exterior surface of the hub when the medical unit is inserted into the locator funnel and aperture to rotate the needle hub and remove the needle assembly from the medical device.

The removal and disposal device may also be provided with additional apertures with wedge shaped portions for removal and disposal of friction retention hubs and for disposal of miscellaneous medical sharps. Such apertures may also be provided with cutting blades for cutting butterfly tubing.

These and other objects of the present invention will become more readily appreciated and understood from a consideration of the following detailed description of the preferred embodiment when taken together with the accompanying drawings in which:

DETAILED DESCRIPTION OF THE INVENTION

Figure 1:
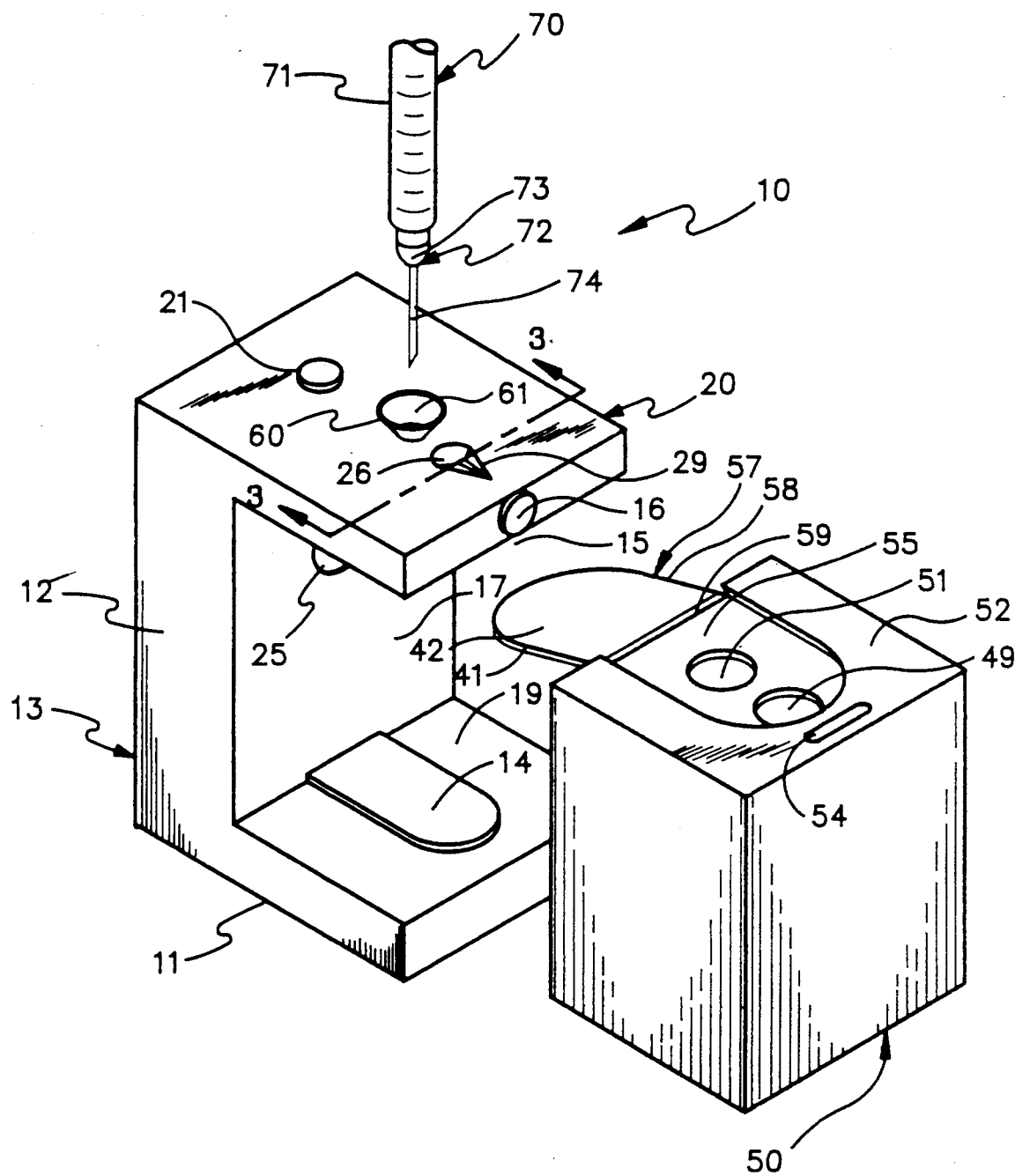
FIG. 1 is a perspective view of the removal and disposal device of the present invention showing the container removed and the container lid partially open.

A medical needle removal and disposal device 10, comprising an exemplary preferred embodiment of the present invention, is illustrated in FIG. 1. Removal and disposal device 10 comprises a base assembly 13, head structure 20 and sealable container 50. Head assembly 20 includes power switch 21 and conical guide member 60. As may be seen in FIG. 2, in the exemplary preferred embodiment, conical guide me 60 converges to an aperture 61. Guide member 60 may be formed of any suitably hard material, preferably of stainless steel or other metal to resist the damage by sharp needle points.

Figure 2:
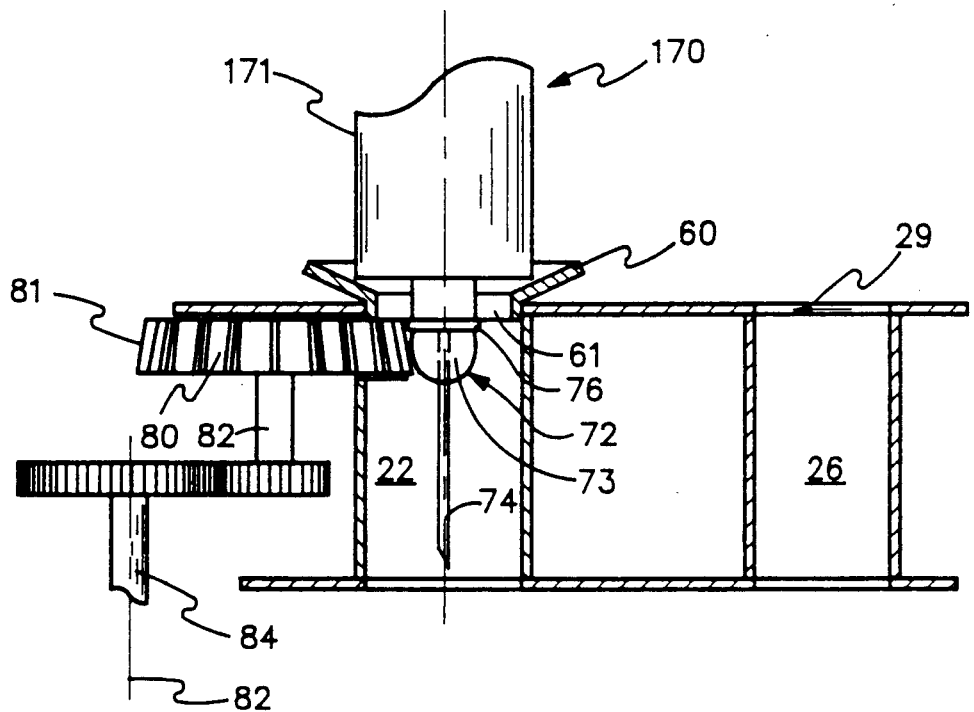
FIG. 2 is a sectional view of a first embodiment showing a medical unit in position for needle assembly removal by the device.

A rotatable member 80 is located beneath the aperture 61 and has an exterior surface 81 encircling an axis of rotation 82 which is parallel to and spaced apart from the axis about which the interior surface of conical guide member 60 converges. The exterior surface 81 of rotatable member 80 of the preferred embodiment is of frusto conical shape, but a cylindrical external surface, or a surface which is rounded in cross-section, may also be utilized. The rotatable member 80 is connected to a drive mechanism including an electric motor or other suitable power device by drive shaft 84. The drive motor may be energized to rotate rotatable member 80 in a counterclockwise direction as viewed in plan from above the pressing power switch 21. The relationship between a diameter of rotatable member 80 and the spacing between the axis of rotation 82 and the axis of convergence 82 is chosen such that, when the needle assembly 72 attached to the medical device 171 of medical unit 170 in FIG. 2, is inserted into guide member 60 and through the orifice 61, an exterior surface of the hub 73 of the needle assembly 72 is urged into contact with exterior surface 81 of rotatable member 80. Power switch 21 may then be pressed to cause rotation of rotatable member 80 and, as rotatable member 80 and hub 73 are coupled by their surface contact, in turn cause rotation of hub 73 in the opposite direction until hub 73 becomes detached from medical device 171. The removal and disposal device of the present invention is suitable not only for use with hubs and medical devices incorporating helical threads but also for loosening the friction lock of friction retention hubs to effect their removal.

Figure 3:
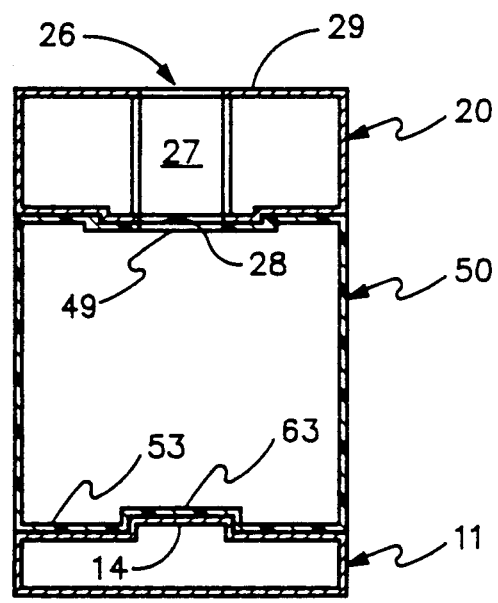
FIG. 3 is a sectional view of the needle assembly removal and disposal device taken in its receptacle position at section line III—III with the enclosure container.
Figure 4A:
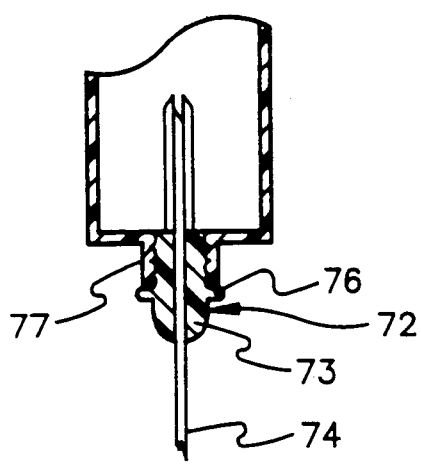
FIGS. 4a 4b, and 4d illustrate four different common hub assemblies.
Figure 4B:
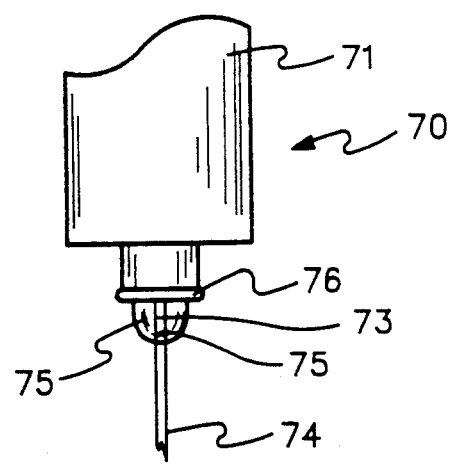
Figure 4C:
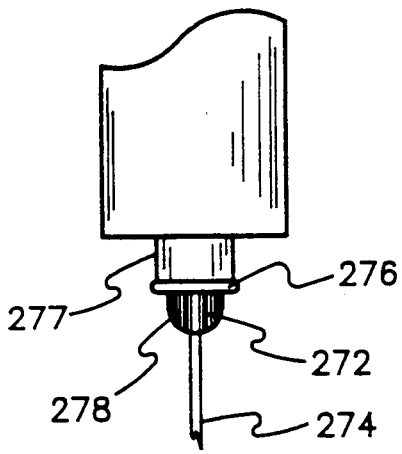
Figure 4D:
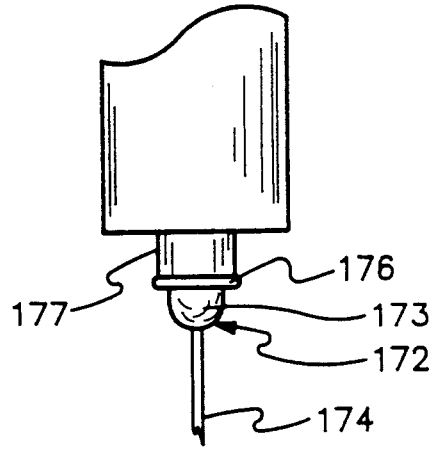

In the exemplary preferred embodiment, a vertical passageway 22 is provided beneath orifice 61 which ends in an opening 23 at the bottom of head structure 20. Container 50 is sized to be insertable between base 11 and head structure 20, and is provided with a primary aperture 51 through its loop panel 52. As may best be seen in FIG. 3, base panel 53 of container 50 of the exemplary appliance 10 is provided with a groove 63 to cooperate with tongue 14 of top surface 19 of base 11 and top panel 52 is provided with a groove 54 to cooperate with a releasable latching device 15, such as is well known in the art, and which may be released by pressing latch button 16. When container 50 is inserted between base 11 and head structure 20, it is held in its receptacle position by cooperation of tongue 14 on top surface 18 of base 11 with the groove of base panel 53, abutment with locating surface 17 pillar structure 12, and the bottom of head structure 20 and cooperation of latch device 15 with groove 54. Primary aperture 51 is so positioned in top panel 52 that, when container 50 is in the receptacle position, aperture 51 is in alignment with hole 23. Thus, with container 50 in the receptacle position, when needle assembly 73 becomes detached from medical device 171 it will pass through passage 22, hole 23 and aperture 51 and become enclosed in container 50. Once container 50 has been filled to its capacity with needle assemblies, container 50 maybe removed from removal and disposal device 10 by passing release button 16 and withdrawing container 50 from between base 11 and head structure 20.

Three common configurations for needle assembly hubs are illustrated in FIG. 4. The most common hub, shown as part of a phlebotomy needle assembly attached to a vacuum via guide device in FIG. 4a in section and b in plan, has four bracing ribs 75 defining a generally cylindrical shape extending away from the attached medical device 71 of the medical unit 70 along needle 74. The hub may also have a fuller shape with longitudinal surface ribs 278 as in the case of hub 273 in FIG. 4c, or a smooth rounded surface as in the case of hub 173 of FIG. 4d. Hubs of needles assemblies presently available generally have a collar 76 which seats against an extension 77 of the medical device.

Rotatable member 80 of the exemplary removal and disposal device 10 has raised ribs 86 an outer surface 81 to engage bracing ribs 75 of hub 73 or longitudinal ribs of hub 273. Further, passageway 22 is of sufficient diameter to allow collar 76 to pass between the outer surface 81 of rotatable member 80 and the inside wall of passage 22.

Figure 5A:
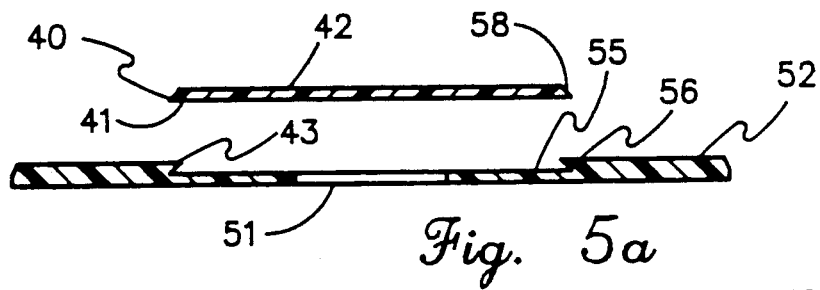
FIGS. 5a and 5b are sectional views of the enclosure container top panel and lid.
Figure 5B:
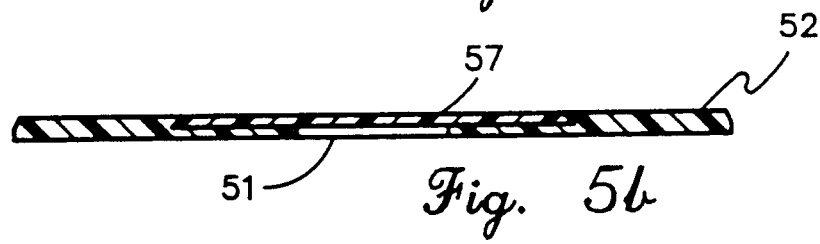

Top panel 52 of container 50 has a recessed portion with a floor 55 and a recess perimeter 56, and a lid 57 with a lid perimeter 58. Lid 57 is hinged to top panel 52 along a rear edge portion of the panel by hinge 59. Lid 57 has an edge wall 40 about its perimeter 58 which extends from an inner lid surface 41 to outer lid surface 42. As may best be seen in FIG. 5, in the preferred embodiment of the exemplary removal and disposal device 10, inner surface 41 of lid 57 is similarly shaped but larger than outer lid surface 42 such that the edge wall 40 of lid 57 forms an acute angle with inner surface 41 and an obtuse angle with outer lid surface 42. A perimeter wall 43 at the perimeter of the recess area as sloped inwardly in an outward direction from floor 55, to form an acute angle with recess floor 55 generally equal to the acute angle formed between edge wall 40 and inner surface 41 of lid 57. Lid 57 and top panel 52 of the exemplary embodiment are fabricated of a material of sufficient softness and elasticity that lid 57 may be rotated about hinge 59 until inner surface 44 of lid 57 abuts floor 55 of the recessed area and the edge wall of lid 57 may be pressed down to seat beneath perimeter wall 43 of the recessed area thereby fixing the perimeter of lid 57 in a closed position sealing aperture 51.

The head structure 20 of the preferred embodiment of needle assembly removal and disposal device 10 may include a downwardly protruding portion 24 in its bottom surface 18 to cooperate with perimeter wall 43 of panel 52 in the manner of a tongue and groove to assist in maintaining aperture 51 of container 50 in alignment with passageway opening 23 when container 50 is in the receptacle position between base 11 and head structure 20. A relieved area 25 may also be provided in surface 17 of pillar structure 12 to cooperate with lid 57 when lid 57 is rotated to a fully open position about hinge 59 and container 50 is in the receptacle position between base 11 and head structure 20 in abutting relation with pillar structure 12 to assist in maintaining container 50 is proper position via hinge 59.

Power switch 21 of the preferred embodiment of removal and disposal device 10 is preferably located in a position to be conveniently depressed with the side of the hand or one of the two outside fingers of the hand while holding a medical unit 70, such as the syringe of FIG. 1, in position with hub 73 of needle assembly 72 in position for needle assembly 72 to be removed by coupling with rotating member 80. While a push switch 21 is used in the preferred embodiment of removal and disposal device 10, a pressure sensitive switch associated with guide member 60, a photosensor positioned at aperture 61, or other control means such as are well known in the art may also be utilized to energize the drive device and rotate member 80 when hub 73 of needle assembly 72 is in position for needle assembly removal.

Head assembly 20 of the exemplary preferred embodiment of removal and disposal appliance 10 is also provided with an additional aperture 26 and a passage way 27 leading to an opening 28 which, when container 50 is in the receptacle position between base 11 and head structure 20, aligns with a second openings 49 of recess area 55 of top panel 52 to provide for the disposal of medical sharps and other small contaminated medical items into container 50. Passage 27 is of sufficiently small diameter and of sufficient length to reduce the likelihood of access by a finger to a contaminated needle which may be in the container 50. Aperture 26 may be provided with converging cutting blades 29 for cutting butterfly tubing and the like.

Figure 6:
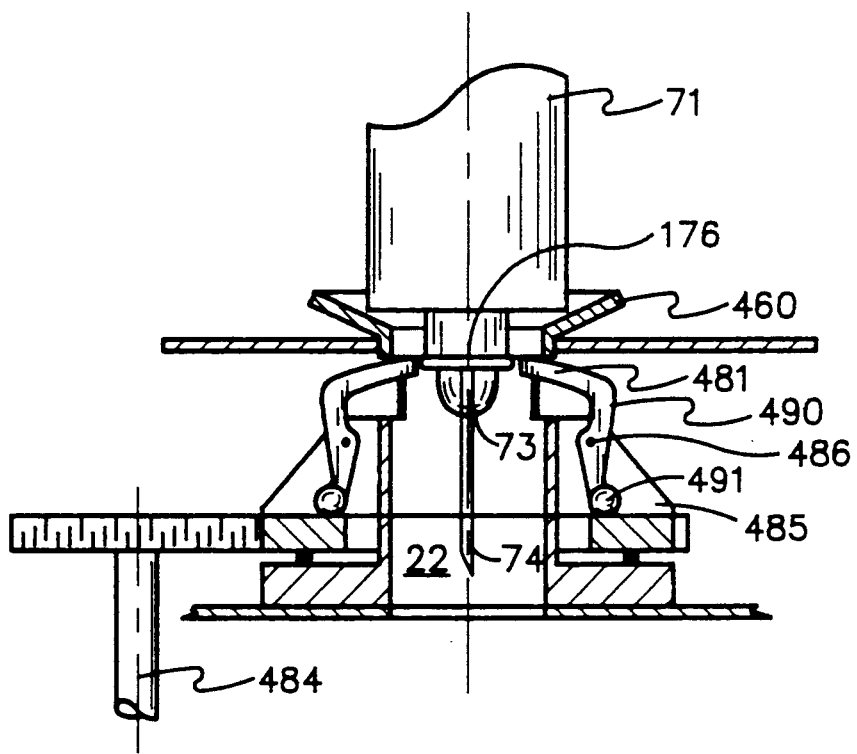
FIG. 6 is a sectional view of a second embodiment of the present invention.

An alternative embodiment of the removal and disposal appliance 10 is illustrated in FIG. 6. In the embodiment of FIG. 6, rotatable member 480 has a generally annular shape with a central aperture 487 through which passes an axis of rotation 482. Rotatable member 480 is mounted on an annular bearing 488 and provided with external gear teeth 484 for engagement with driver gear 489 which annular rotatable member 480 of the embodiment of FIG. 6 includes support ears 485. Jaws 490 are supported by ears 485 at hinge points 486. Jaws 490 comprise mass concentration 491 such that, when rotatable member 480 is in response, the center of gravity of jaws 490 is located radially outwardly and below hinge point 86. Thus when the motor of the drive mechanism is activated to rotate member 480 about axis of rotation 482 jaws 490 rotate about hinge points 486, due to centrifugal force, and coupling portions 481 of jaws 490 are moved inward toward the axis of rotation 482. Conical guide member 460 and guide aperture 461 are located above central aperture 487 of rotatable member 480 with axis of convergence 483 coinciding with axis of rotation 482. Aperture 461 is located at such a height above rotatable member 480 that coupling portions 481 will close upon hub 473 when rotatable member 480 is rotated to couple hub 473 to rotatable member 480 and cause hub 473 to rotate and detach from medical device 471. Once hub 473 has become detached from medical device 471, rotation of rotatable member 480 may be ceased by releasing power switch 21 to return jaw member 490 to its position of repose clear of collar 476 to release the needle assembly 472 and allow it to fall through passage 422 and opening 423 and on into container 50 below. While, in the preferred embodiment of FIG. 4, a plurality of coupling portions move relative to axis of rotation 482, some of the coupling portions may be fixed in relation to annular rotatable member 480. Further, while coupling portions 481 of the preferred embodiment of FIG. 4 move in response to centrifugal forces, other chuck jaw mechanisms may be used which are well known in the art, such as those which work on a principal of annular momentum or are activated by electrical or mechanical drives.

Figure 7A:
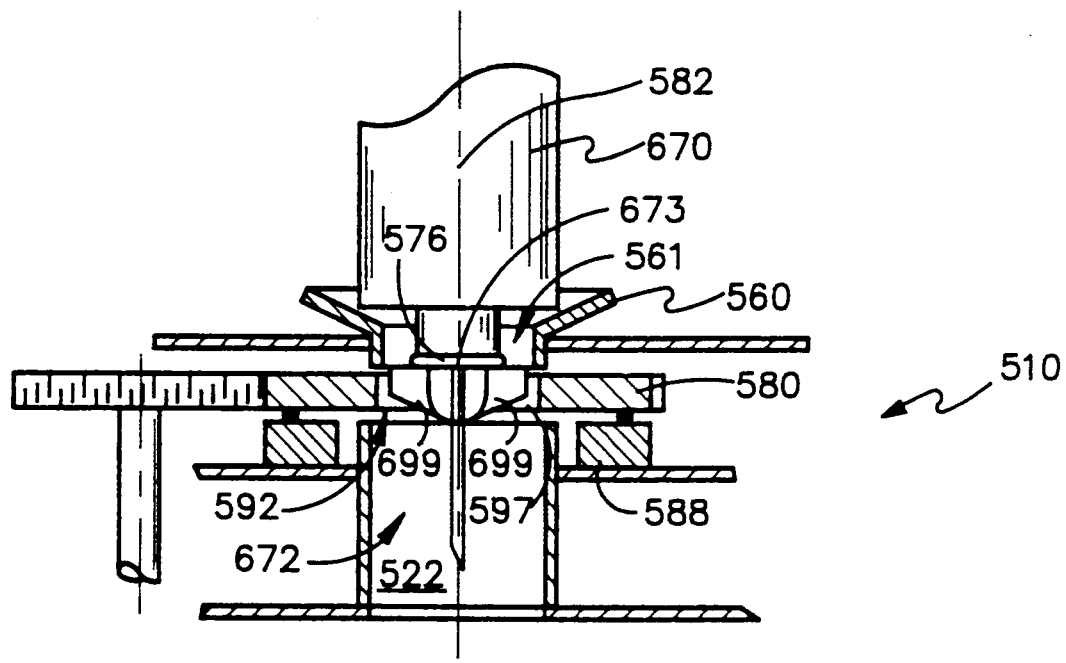
FIGS. 7a and 7b are sectional and end views of a third embodiment of the present invention.
Figure 7B:
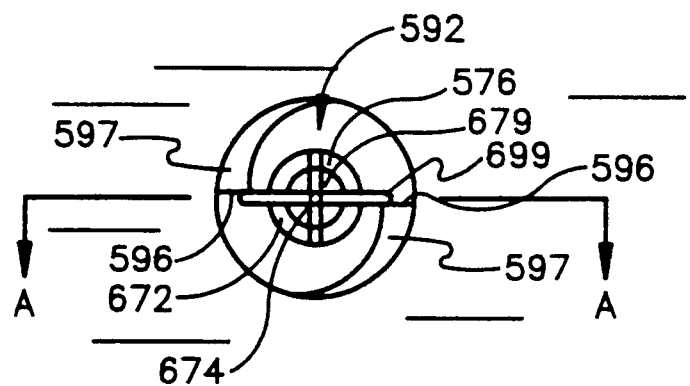
Figure 8:
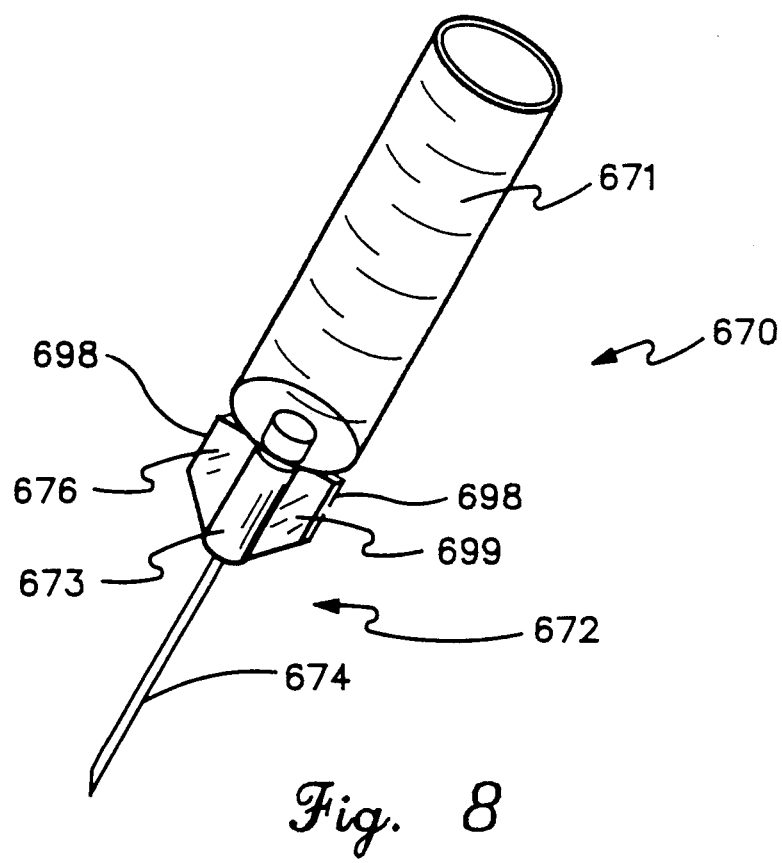
FIG. 8 is a perspective view of a syringe medical unit having a winged needle assembly.

A second alternative embodiment of a removal and disposal device 510 is illustrated in FIG. 7. The embodiment of FIG. 7 is intended for use with a needle assembly such as 672 illustrated in FIG. 8. The needle assembly 672 of syringe 670 comprises a threaded hub 673 and a needle 674. The threaded hub 673 has lugs in the form of wings 699 which extend outwardly from a longitudinal hub axis beyond the outer extremities of collar 676 to end in free ends 698.

Rotatable member 580 is of an annular shape with an internal surface defining a central aperture 592 and is mounted on an annular bearing 588 to rotate about an axis of rotation 582 passing through the center of aperture 592. Conical guide member 560 and guide aperture 561 are located above the central aperture 592 with the axis of guide member 560 and aperture 561 coinciding with the axis of rotation 582. Aperture 561 is at such a height above rotating member 580 that when the needle assembly 672 of medical unit 670 is inserted into concical guide member 560 and guide aperture 561, hub 673 is suspended within the aperture 592 of rotatable member 580. Coupling extensions 597 extend inwardly toward the axis of rotation from the interior surface of aperture 592 of rotating member 580 a sufficient distance for coupling portion 596 to act against distal ends 698 of wings 699 when rotatable member 580 is rotated and to rotate hub 673 to disengage needle assembly 672 from medical device 670. Coupling extension 597 extends inwardly of aperture 592 only to a point where the inner distance between the inner most portions of opposing coupling surfaces 596 is greater than the diameter of collar 576. This allows needle assembly 572 to fall through aperture 592, passage way 522 and opening 523 once it becomes detached from medical device 670.

While an exemplary removal and disposal device embodying the present invention has been shown, it will be understood, of course, that the present invention is not limited to that embodiment. Modification may be made by those knowledgeable of the art, particularly in light of the foregoing teachings. For example, coupling surfaces to act upon the distal end portions of the hub wings of the hub of the needle assembly of FIG. 6 might be provided by the coupling portions of centrifugal jaws. It is, therefore, contemplated by the appended claims to cover any such modification which incorporates the central features of this invention or encompasses the true spirit and scope of the invention.

I claim:

1. An apparatus for removing and disposing of needle assemblies used in combination with medical devices wherein each needle assembly includes a needle portion with a sharp end and a base end, the base end including a hub of generally cylindrical shape, each said hub adapted for cooperative engagement with the medical device to attach the respective needle assembly to the respective medical device for use in combination with the medical device as a medical unit, the apparatus operative to remove needle assemblies having different sized hubs and comprising:
   hub rotating means including a rotating member having an outer surface surrounding an axis of rotation adapted for coupling with and rotating hubs of varying diameter at varying distances from said axis of rotation about the longitudinal axis of each respective said hub to cause the respective needle assembly to become detached from the medical device of the medical unit;
   hub locator means for maintaining the hub of the needle assembly of the medical unit in a fixed spacial location and orientation in which said hub is coupled with the outer surface of said rotating member to cause the needle assembly to rotate and become detached from the medical device of the medical unit; and
   enclosure means for receiving and protectively enclosing the needle assembly after it is detached from the medical device.

2. The removal and disposal apparatus of claim 1 in which said hub rotating means comprises a rotating member having an outer surface surrounding an axis of rotation and said locator means includes means for maintaining the hub in a location in which an exterior surface of the hub is in contact with said outer surface of said rotating member and in an orientation in which the longitudinal axis of the hub is generally parallel to said axis of rotation.

3. The removal of disposal apparatus of claim 2 in which said outer is a frusto conical surface.

4. The removal and disposal apparatus of claim 3 further comprising:
   drive mechanism means for causing said rotating member to rotate, said drive mechanism means including power switching means for energizing said drive mechanism means on demand.

5. The removal and disposal apparatus of claim 4 in which said switching means comprises sensing means for sensing when the hub is in said location and orientation and energizing said drive mechanism means only when the hub is in said location.

6. The removal and disposal apparatus of claim 2 in which the exterior surface of the hub includes a plurality of longitudinal hub ribs generally parallel to the longitudinal axis and said outer surface of said rotating member comprises a plurality of driving ribs each rib arranged generally in a plane in common with said axis of rotation, said driving ribs adapted to engage said hub ribs when the exterior surface of the hub is in contact with said outer surface of said rotating member.

7. The removal and disposal apparatus of claim 2 in which said hub locator means comprises a guide member, said guide member including a generally frusto conical inner guide surface defining an aperture for receiving the needle assembly of a medical unit, said frusto conical surface converging along an axis extending from said aperture, said axis located in proximity to said outer surface of said rotating member such that, when the needle assembly of the medical unit is inserted through said aperture said guide surface urges the exterior surface of the hub of the needle assembly into contact with said outer surface.

8. The removal and disposal apparatus of claim 1 in which said enclosure means comprises:

container means having a flat top panel, said panel surrounding an aperture of sufficient size for a needle assembly to pass therethrough, a lid of sufficient size to cover said aperture, retention means for engaging and retaining said lid in a fixed position when it is placed over said aperture and releasable position fixing means for releasably fixing said container means in a receptacle position in which the needle assembly will pass through said aperture when the needle assembly has become detached from the medical device of the medical unit.

9. The removal and disposal apparatus of claim 8, further comprising:

a head structure for supporting and housing said hub rotating means and said hub locator means, said head structure having a bottom surface;

a base structure having a top surface, said top surface including a raised tongue;

a pillar structure rigidly attached to said head and said base in such a manner as to maintain said bottom surface and said top surface in fixed, set apart parallel relation and said container in a top panel and a base panel, and said releasable position fixing means comprises said base panel has a groove sized to cooperatively receive said tongue, said container is sized to be insertable between said head and said base to a receptacle position in which said top panel abuts said bottom surface and said base panel abuts said top surface and said tongue is cooperatively and slidingly received within said groove; and latch means for releasably retaining said container in a position along said tongue when said container is in said receptacle position.

10. A removal and disposal apparatus as in claim 9 in which said top panel includes a recess portion and said bottom surface further comprises a protruding portion said protruding portion sized to cooperatively engage said recess portion when said container is in said receptacle position.

11. The removal and disposal apparatus of claim 10 in which said top panel includes a back edge portion and said container includes a lid, said lid hingedly attached to said back edge portion to rotate between a closed position in which said lid covers said aperture and an open position and said pillar structure includes a locating surface having a recess portion, said recess portion sized and shaped to cooperatively receive said lid when said lid is in the open position and said container is in said receptacle position.

12. A removal and disposal apparatus as in claim 8 in which said lid has a lid perimeter and said top panel includes a recess portion surrounding said aperture said recess portion having a recess perimeter of a shape and size the same as the shape and size of said lid perimeter, said recess perimeter having lid perimeter engagement means for engaging said lid perimeter when said lid is covering said aperture.

13. The removal and disposal apparatus of claim 12 in which said top panel includes a back edge portion and said lid is hingedly attached to said back edge portion.

14. The removal and disposal apparatus of claim 13 in which said recessed portion has a planar floor and a recess wall at its perimeter, said lid is planar and has an interior surface which abuts said floor when said lid is covering said aperture, an exterior surface on a side of said lid opposite from said interior surface, and an edge wall at said lid perimeter, said edge wall extending from said exterior surface to said interior surface, and said perimeter engagement means comprises said exterior surface is smaller than said interior surface such that said edge wall forms an acute angle with said interior surface and an obtuse angle with said exterior surface and said recess wall forms an acute angle with said recess floor.

15. An apparatus for removing and disposing of needle assemblies used in combination with medical devices, the needle assembly including a needle portion with a sharp end and a base end, the base end including a hub of generally cylindrical shape, the hub adapted for cooperative engagement with a medical device to attach the needle assembly to the medical device for use in combination with the medical device as a medical unit, the apparatus comprising:

a head structure including means for removing the hub from the medical device of the medical unit; and a container adapted to fit beneath said head structure to receive said needle assembly upon removal of said needle assembly from said medical device for protectively enclosing a needle assembly, the container including a flat top panel, having a back edge portion and a recess portion, said recess portion surrounding an aperture of sufficient size for a needle assembly to pass therethrough and having a planar floor and a recess wall at a recess perimeter forming an acute angle with said recess floor and a planar lid hingedly attached to said back edge portion, said lid having a lid perimeter of a shape and size the same as the shape and size of said recess perimeter, an interior surface which abuts said floor when said lid is in a closed position in which said lid covers said aperture, an exterior surface on a side opposite from said interior surface, and an edge wall at the lid perimeter extending from said interior surface to said exterior surface, said exterior surface being smaller than said interior surface such that said edge wall forms an acute angle with said interior surface and an obtuse angle with said exterior surface whereby said lid perimeter is held in fixed engagement at said recess perimeter when said lid is covering said aperture.

16. Apparatus for facilitating the removal and disposal of a needle assembly used in combination with a medical device as a medical unit, the needle assembly including a needle portion with a sharp end and a base end, the base end including a hub of generally cylindrical shape, the hub having at least one lug extending radially outwardly to a free distal end, said hub adapted for cooperative engagement with the medical device to attach the needle assembly to the medical device for use in combination with the medical device as a medical unit, the apparatus comprising:

a housing structure having an upper aperture through which the needle assembly may be inserted;

hub rotating means in said housing structure and rotatable about a fixed axis of rotation for engaging said lug to rotate the hub about its longitudinal axis thereby causing the needle assembly to become detached from the medical device of the medical unit;

guide means including a conical guide member surrounding said aperture and extending upwardly therefrom for guiding differently sized medical devices in order to center a respective hub thereof along a common hub axis parallel to said fixed axis of rotation to orient each respective hub in a position for engagement by said hub rotating means; and enclosure means for receiving and protectively enclosing the needle assembly after it is detached from the medical device.

17. An apparatus for facilitating the removal and disposal of a needle assembly as in claim 21 in which said hub rotating means includes an inner surface defining an aperture about said axis of rotation and lug engagement means extending inwardly towards said axis of rotation from said inner surface for engaging said lug means with the hub axis coinciding with said axis of rotation, whereby, when said hub rotating means is rotated, said hub rotating means and said hub are coupled to rotate together about a common axis.

18. The apparatus for facilitating the removal and disposal of needle assemblies as in claim 16, in which said hub rotating means includes lug engagement means which extends inwardly toward said axis of rotation to engage said lug when said rub rotating means is rotated and retracts outwardly away from said axis of rotation when said hub rotating means is at rest.

19. An apparatus for removing and disposing of needle assemblies used in combination with medical device, the needle assembly including a needle portion with a sharp end and a base end, the base end including a hub of generally cylindrical shape, the hub adapted for cooperative engagement with the medical device to attach the needle assembly to the medical device for use in combination with the medical device as a medical unit, the apparatus comprising:

a base adapted to rest on a support surface;

a head structure connected to and supported in spaced relation to said base, said head structure including hub rotating means for coupling with and rotating the hub about its longitudinal axis to cause the needle assembly to become detached from the medical device of the medical unit;

hub locator means for maintaining the hub of the needle assembly of the medical unit in a fixed spacial location and orientation in which said hub is coupled with said hub rotating means to cause the needle assembly to rotate and become detached from the medical device of the medical unit;

enclosure means insertable between said base and said head structure and supported thereby, said enclosure means for receiving and protectively enclosing the needle assembly after it is detached from the medical device; and releasable position fixing means for releasably fixing said enclosure means in a receptacle position in which the needle assembly will pass through said aperture when the needle assembly has become detached from the medical device of the medical unit.

20. A removal and disposal apparatus as in claim 19 in which said hub rotating means comprises a member rotatable about an axis of rotation and said hub locator means comprises an aperture defined by an interior surface of said rotatable member about said axis of rotation and said rotatable member further comprises coupling means for coupling the hub of the needle assembly with said rotatable member when the hub is positioned with the longitudinal hub axis coinciding with the axis of rotation.

21. The removal and disposal apparatus of claim 20 wherein said hub has a longitudinal rib parallel to the hub axis and said coupling means comprises a coupling element protruding into said aperture from said interior surface.

22. The removal and disposal apparatus of claim 20 in which said coupling means comprises chuck means for closing about and clamping the hub when said rotatable member is rotated.

23. The removal and disposal apparatus of claim 22 in which said chuck means includes a jaw element movably attached to said rotatable member such that a portion of said jaw element maintaining a first position of repose at a first distance from said axis of rotation when said rotatable member is at rest and maintains a coupling position a smaller distance from said axis of rotation when said rotatable member is rotated.

24. A removal and disposal apparatus as in claim 23 in which said jaw element is pivotably mounted at a pivot point on said rotatable member, said jaw element has a center of gravity located a distance apart from said jaw portion when measured in a direction parallel to said axis of rotation and said pivot point lies between said jaw portion and said center of gravity along said direction such that, when said rotatable member is rotated said center of gravity tends to move outwardly from said axis of rotation and said jaw portion is caused to move inwardly toward said axis of rotation.

* * * * *